(12) United States Patent
Tearney et al.

(10) Patent No.: US 10,095,020 B2
(45) Date of Patent: Oct. 9, 2018

(54) APPARATUS AND METHODS FOR COLOR ENDOSCOPY

(71) Applicants: CANON U.S.A., INC., Melville, NY (US); THE GENERAL HOSPITAL CORPORATION, Boston, MA (US)

(72) Inventors: Guillermo J. Tearney, Cambridge, MA (US); Dongkyun Kang, Somerville, MA (US); Mitsuhiro Ikuta, Cambridge, MA (US)

(73) Assignees: Canon U.S.A., Inc., Melville, NY (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/115,484

(22) PCT Filed: Jan. 30, 2015

(86) PCT No.: PCT/US2015/013788
§ 371 (c)(1),
(2) Date: Jul. 29, 2016

(87) PCT Pub. No.: WO2015/116939
PCT Pub. Date: Aug. 6, 2015

(65) Prior Publication Data
US 2017/0168232 A1 Jun. 15, 2017

Related U.S. Application Data

(60) Provisional application No. 61/934,464, filed on Jan. 31, 2014.

(51) Int. Cl.
*G02B 23/26* (2006.01)
*A61B 1/07* (2006.01)
(Continued)

(52) U.S. Cl.
CPC ...... *G02B 23/2469* (2013.01); *A61B 1/00096* (2013.01); *A61B 1/07* (2013.01);
(Continued)

(58) Field of Classification Search
None
See application file for complete search history.

(56) References Cited

U.S. PATENT DOCUMENTS 3,976,360 A 8/1976 Schroder
4,074,306 A 2/1978 Kakinuma et al.
(Continued)

FOREIGN PATENT DOCUMENTS

CN 103424799 A 12/2013
JP 2011527930 A 11/2011
(Continued)

OTHER PUBLICATIONS

Yun, et al., "High-speed spectral-domain optical coherence tomography at 1.3 μm wavelength", Opt Express, Dec. 29, 2003, pp. 3598-3604, No. 11, vol. 26.
(Continued)

*Primary Examiner* — Michelle R Connelly
(74) *Attorney, Agent, or Firm* — Canon USA, Inc., IP Division

(57) ABSTRACT

A probe can be provided having a grating adapted for color spectrally encoded imaging. The probe can include a waveguide configuration, a light focusing configuration, and a grating configuration that can have a first grating pattern and a second grating pattern. The waveguide configuration can be configured and/or structured to cause to propagate a light having a first wavelength and a light having a second wavelength to propagate from the waveguide component, and the light focusing and waveguide configurations can provide the light to be incident on the grating configuration.

(Continued)

The grating configuration can be configured and arranged such that the light having the first wavelength is diffracted by the first grating pattern to substantially the same location as the light having the second wavelength is diffracted by the second grating pattern.

15 Claims, 8 Drawing Sheets

(51) Int. Cl.
| | | |
|---|---|---|
| G02B 6/06 | (2006.01) | |
| G02B 23/24 | (2006.01) | |
| A61B 1/00 | (2006.01) | |
| G02B 6/02 | (2006.01) | |
| G01J 3/18 | (2006.01) | |
| G01J 3/02 | (2006.01) | |
| G02B 6/24 | (2006.01) | |
| G02B 6/293 | (2006.01) | |

(52) U.S. Cl.
CPC ............ *G01J 3/0208* (2013.01); *G01J 3/0218* (2013.01); *G01J 3/1895* (2013.01); *G02B 6/02076* (2013.01); *G02B 6/02085* (2013.01); *G02B 23/24* (2013.01); *G02B 23/2423* (2013.01); *G02B 23/26* (2013.01); *G02B 6/241* (2013.01); *G02B 6/29311* (2013.01)

(56) References Cited

U.S. PATENT DOCUMENTS

| | | | |
|---|---|---|---|
| 4,264,127 A | | 4/1981 | Schumacher et al. |
| 5,565,983 A | | 10/1996 | Barnard |
| 6,341,036 B1 | | 1/2002 | Tearney et al. |
| 6,485,413 B1 | | 11/2002 | Boppart et al. |
| 6,488,414 B1* | | 12/2002 | Dawes ................... G02B 6/241 385/141 |
| 6,522,403 B2* | | 2/2003 | Wilson ...................... G01J 3/02 356/328 |
| 6,661,513 B1 | | 12/2003 | Granger |
| 6,831,781 B2 | | 12/2004 | Tearney et al. |
| 6,858,859 B2 | | 2/2005 | Kusunose |
| 7,003,196 B2 | | 2/2006 | Ghiron |
| 7,181,106 B2* | | 2/2007 | Ushiro .................. G02B 5/1857 359/566 |
| 7,551,293 B2 | | 3/2009 | Yelin et al. |
| 7,796,270 B2 | | 9/2010 | Yelin et al. |
| 7,843,572 B2 | | 11/2010 | Tearney et al. |
| 7,859,679 B2 | | 12/2010 | Bouma et al. |
| 7,894,058 B2* | | 2/2011 | Wilson ...................... G01J 3/02 356/328 |
| 8,000,775 B2 | | 8/2011 | Pogue et al. |
| 8,045,177 B2 | | 10/2011 | Tearney et al. |
| 8,145,018 B2 | | 3/2012 | Shishkov et al. |
| 8,203,708 B2 | | 6/2012 | Lee et al. |
| 8,289,522 B2 | | 10/2012 | Tearney et al. |
| 8,446,593 B1 | | 5/2013 | Ellerbee |
| 8,780,176 B2 | | 7/2014 | Yelin |
| 8,792,757 B2 | | 7/2014 | Boudoux et al. |
| 8,804,133 B2 | | 8/2014 | Yelin et al. |
| 8,812,087 B2 | | 8/2014 | Yelin et al. |
| 8,818,149 B2 | | 8/2014 | Shishkov et al. |
| 8,838,213 B2 | | 9/2014 | Tearney et al. |
| 9,254,089 B2 | | 2/2016 | Tearney et al. |
| 2002/0114566 A1 | | 8/2002 | Fairchild et al. |
| 2002/0122246 A1 | | 9/2002 | Tearney |
| 2002/0145815 A1 | | 10/2002 | Moriyama et al. |
| 2003/0142934 A1 | | 7/2003 | Pan et al. |
| 2004/0147810 A1 | | 7/2004 | Mizuno |
| 2005/0155704 A1 | | 7/2005 | Yokajty et al. |
| 2007/0188855 A1* | | 8/2007 | Shishkov ............. A61B 5/0062 359/362 |
| 2007/0233396 A1 | | 10/2007 | Tearney et al. |
| 2008/0013960 A1 | | 1/2008 | Tearney et al. |
| 2008/0097225 A1* | | 4/2008 | Tearney ................. A61B 18/22 600/478 |
| 2009/0141360 A1 | | 6/2009 | Koyama |
| 2010/0210937 A1 | | 8/2010 | Tearney et al. |
| 2011/0237892 A1* | | 9/2011 | Tearney ............... A61B 5/0062 600/160 |
| 2011/0275899 A1 | | 11/2011 | Tearney et al. |
| 2012/0025099 A1 | | 2/2012 | Yelin et al. |
| 2012/0112094 A1 | | 5/2012 | Kao et al. |
| 2012/0328241 A1* | | 12/2012 | Shishkov ............. A61B 5/0062 385/35 |
| 2013/0012771 A1 | | 1/2013 | Robertson |
| 2013/0310643 A1 | | 11/2013 | Gora et al. |
| 2014/0071238 A1* | | 3/2014 | Mertens .................... A61B 1/07 348/45 |
| 2014/0285878 A1 | | 9/2014 | Escuti et al. |
| 2015/0045622 A1 | | 2/2015 | Shishkov et al. |
| 2015/0105622 A1* | | 4/2015 | Yelin .................... A61B 5/0084 600/182 |
| 2015/0231841 A1* | | 8/2015 | Tearney ........... B29D 11/00663 156/247 |
| 2016/0206184 A1* | | 7/2016 | Tearney ............... A61B 5/0062 |
| 2016/0341951 A1* | | 11/2016 | Tearney ............. A61B 1/00096 |
| 2016/0349417 A1* | | 12/2016 | Tearney ............... G02B 5/1814 |

FOREIGN PATENT DOCUMENTS

| | | |
|---|---|---|
| JP | 2013056165 A | 3/2013 |
| JP | 2013544151 A | 12/2013 |
| WO | 2013108209 A1 | 7/2013 |
| WO | 2014031748 A1 | 2/2014 |
| WO | 2014104405 A1 | 7/2014 |
| WO | 2015116939 A1 | 8/2015 |
| WO | 2015116951 A2 | 8/2015 |
| WO | 2015116974 A1 | 8/2015 |

OTHER PUBLICATIONS

Zeidan, A., et al., "Miniature forward-viewing spectrally encoded endoscopic probe", Optics Letters, Aug. 15, 2014, pp. 4871-4874, vol. 39, Issue 16.

Pitris, C., et al., "A GRISM-based probe for spectrally encoded confocal microscopy", Optics Express, Jan. 27, 2003, pp. 120-124, vol. 11, No. 2.

Yelin, D., et al., "Three-dimentional miniature endoscopy", Nature, Oct. 19, 2006, pp. 765, vol. 443.

Kang, D., et al., "Miniature grating for spectrally-encoded endoscopy," Lab on a Chip, 2013, pp. 1810-1816, vol. 13.

Kang, D., et al., "Spectrally-encoded color imaging", Opt Express, Aug. 17, 2009, pp. 15239-15247, vol. 17, No. 17.

\* cited by examiner

A: 310
B: 320
C: 330

APPARATUS AND METHODS FOR COLOR ENDOSCOPY

CROSS-REFERENCE TO RELATED APPLICATION(S)

This application is a national stage application of PCT/US15/13788 filed 30 Jan. 2015 and claims priority to U.S. Provisional Application Ser. No. 61/934,464 filed Jan. 31, 2014, the content of each of which are incorporated herein by reference in their entirety.

This application relates to U.S. Provisional Application Ser. No. 61/934,486 (Optical probe, light intensity detection, imaging method and system for forward-view imaging), filed Jan. 31, 2014, and to U.S. Provisional Application Ser. No. 61/934,421 (System and method for fabrication of miniature endoscope using nanoimprint lithography), filed Jan. 31, 2014, the entire contents of such disclosures are incorporated herein by reference.

FIELD OF THE DISCLOSURE

The present disclosure relates generally to miniature endoscopes, and more particularly to exemplary apparatus, systems, methods for the fabrication and use of miniature endoscopes that conduct color imaging.

BACKGROUND INFORMATION

Spectrally encoded endoscopy ("SEE") is a technique that uses wavelength to encode spatial information on a sample, thereby allowing high-resolution imaging to be conducted through small diameter endoscopic probes. SEE can be accomplished using a quasimonochromatic or broad bandwidth light input into a single optical fiber. At the distal end of the fiber, a diffractive or dispersive optic disperses the light across the sample, which is reflected and returns back through the optic and optical fiber. Light from the optical fiber is detected by a wavelength detecting apparatus, such as a spectrometer. By detecting the light intensity as a function of wavelength, the image may be reconstructed. SEE techniques have been described in, e.g., U.S. Pat. Nos. 7,843,572, 8,145,018, 6,341,036, 7,796,270 and U.S. Patent Publication Nos. 2008/0013960 and 2011/0237892, the entire contents of which are herein incorporated by reference.

Conventional endoscopy uses RGB color information as cues to diagnosis. By using wavelength information to encode spatial location, SEE images utilize much of the color information to encode spatial location and therefore important color information may be lost. Previously, methods for conducting color imaging in an SEE probe have been proposed. For example, color SEE imaging in a bench top setup has been described (See, e.g., Optics Express, 17(17), 15239-15247; 2009). In this bench top setup, three light beams, each with one of the red, green, and blue spectral bands, were used. These light beams were incident on the grating at different angles, which resulted in same diffraction angle for all three spectral bands. Therefore, each point on the tissue was illuminated with three spectral bands. While this method showed a feasibility of conducting color SEE imaging, implementing this method into a miniature SEE probe has many technological challenges. Three fibers need to be precisely aligned and assembled with the miniature lens. These three fibers generally make the scanning on a SEE probe challenging. In a different approach, color SEE imaging was demonstrated using a single illumination beam (see, e.g., Optics Express, 19(7), 6913-6922; 2011). In this method, each point of the specimen was illuminated with single wavelength, but the specimen was translated relative to the SEE set up. Therefore, each point of the specimen was examined by multiple wavelengths, and the spectral information was used to recover color images of the specimen. This conventional method, however, uses a precise translation of the specimen in a controlled manner, which is not feasible in endoscopic imaging applications.

Accordingly, there may be a need to address and/or overcome at least some of the deficiencies described herein above.

SUMMARY OF EXEMPLARY EMBODIMENTS

According to various exemplary embodiments of the present disclosure, apparatus and methods for color imaging using spectrally encoded endoscopy techniques can be provided. Certain exemplary apparatus and method can retain color information including, for example, a conventional red-green-blue color space.

Thus, according to an exemplary embodiment of the present disclosure, a probe can be provided which can include a waveguide configuration, a light focusing configuration, and a grating configuration that can have a first grating pattern and a second grating pattern. The waveguide configuration can be configured and/or structured to cause to propagate a light having a first wavelength and a light having a second wavelength to propagate from the waveguide component, and the light focusing and waveguide configurations can provide the light to be incident on the grating configuration. The grating configuration can be configured and arranged such that the light having the first wavelength is diffracted by the first grating pattern to substantially the same location as the light having the second wavelength is diffracted by the second grating pattern.

For example, the first grating pattern and the second grating pattern can have different groove densities. The first and second grating patterns can be substantially parallel to each other. The grating configuration can be configured and/or arranged such that the light having a third wavelength is diffracted by a third grating pattern to substantially the same location as the light at the first wavelength and the light at the second wavelength. The first, second and third grating patterns can be substantially parallel to each other. The first and second grating patterns can be repeated at least two times each on the grating configuration. In addition, a detection waveguide can be provided, which can include an optical fiber positioned such that a reflected light reflected by a tissue travels through the grating configuration before it is incident on the detection optical fiber. The portion of the grating configuration provided in front of the detection waveguide can have the first grating pattern and the second grating pattern that are repeated at least two times each. The detection optical fiber can be positioned such that a reflected light reflected by a tissue is incident on the optical fiber without previously traveling through the grating configuration.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which.

Figure 1:
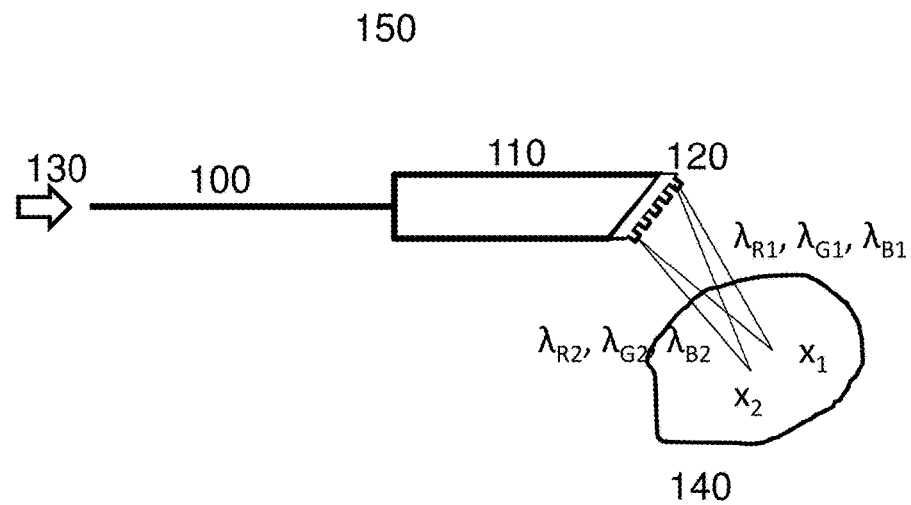
FIG. 1 is a diagram of an exemplary SEE probe according to an exemplary embodiment of the present disclosure.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject disclosure as defined by the appended claims.

DETAILED DESCRIPTION OF EXEMPLARY EMBODIMENTS

A diagram of an exemplary embodiment of the SEE probe is shown in FIG. 1. For example, the SEE probe 150 can include an optical fiber 100, a focusing lens 110, and a diffraction grating 120. Broadband light 130 (or other electro-magnetic radiation) can be delivered to the focusing lens no though the optical fiber 100. The light (or other electro-magnetic radiation) can then be diffracted by the grating 120. This grating 120 can have three or more spatial frequencies for the grating pattern so that each point of the specimen 140 is illuminated by three diffracted light beams, each of which can be included in one of the red (wavelength: 585-660 nm), green (500-575 nm), and blue (415-490 nm) spectra.

Figure 2:
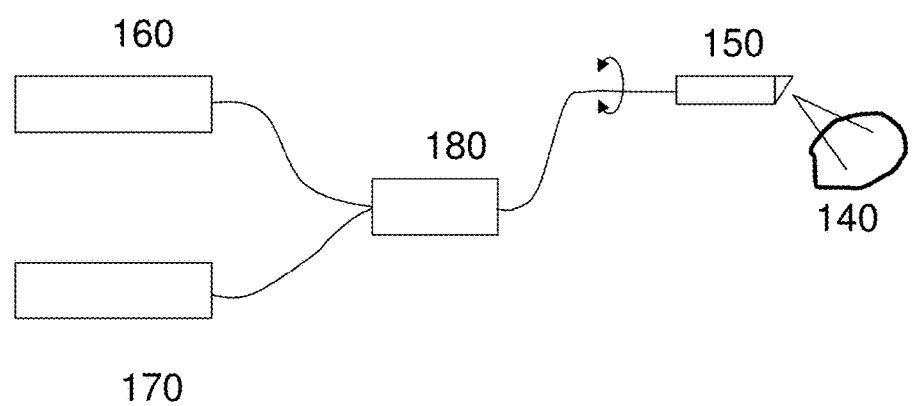
FIG. 2 is a diagram of an exemplary SEE system according to an exemplary embodiment of the present disclosure.

A diagram of an exemplary embodiment of the SEE system that can include the exemplary probe of FIG. 1 is shown in FIG. 2. For example, broadband light from a source 160 (or other electro-magnetic radiation) can be coupled to a coupler 180, and then delivered to the SEE probe 150. Light (or other electro-magnetic radiation) reflected from the specimen 140 can be coupled back to the SEE probe 150, and transferred to the coupler 180. Then, the light (or other electro-magnetic radiation) can be delivered to a spectrometer 170, where the spectrum of the reflected light can be analyzed. The acquired spectrum can be divided into three sub-spectra, each of which represents one of the red, green, and blue spectra. The three sub-spectra can be processed and combined into a single color line image of the specimen. The exemplary SEE probe can be rotationally scanned back and forth to obtain two-dimensional images of the specimen 140.

Figure 3:
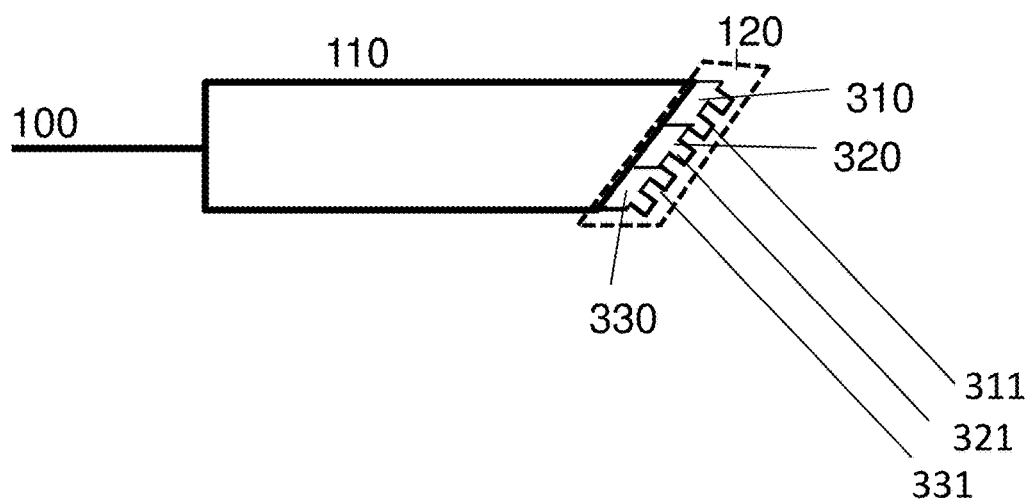
FIG. 3 is a diagram of an exemplary SEE probe according to an exemplary embodiment of the present disclosure.

FIG. 3 shows the exemplary probe (shown in FIG. 1) according to the exemplary embodiment of the present disclosure, in further detail. For example, the grating 120 can have multiple regions that have distinctive groove densities. Groove density parameters of the gratings can be chosen such that such that a light having a first wavelength $\lambda_1$ incident on the grating component from the waveguide component and focused by the light focusing component is diffracted from the first grating region (groove density: $G_1$) to substantially the same location as the diffraction of a light having a second wavelength $\lambda_2$ incident on the second grating region (groove density: $G_2$) from the waveguide component and focused by the light focusing component. If the refractive index of the grating and the incident angle to the grating are the almost the same between for $\lambda_1$ and $\lambda_2$, the relationship of $\lambda_1$, $\lambda_2$, $G_1$, and $G_2$ will be as follows:

$$G_1\lambda_1 \approx G_2\lambda_2.$$

Each region can have a certain number of grooves, for example, 10 grooves, 50 grooves, 100 grooves, 500 grooves, etc. In some exemplary embodiments, the total number of grooves in a region can be at least 100 to maintain sufficient light diffraction from the regions. For example, the three regions in FIG. 3, i.e., regions 310, 320 and 330, can have the groove densities of 1600, 2000, and 2400 lines/mm, respectively such that 675 nm, 540 nm and 450 nm light can be diffracted to the same location on a tissue surface. Each of the regions 310, 320 and 330 can be located in the same plane and has a size that is at least 50 µm×50 µm square.

As discussed herein, the term substantially the same location in the context of two or more light beams incident on a surface at substantially the same location can mean, but not limited to, for example, that the area of the light beams overlaps by at least 50%, at least 70%, or at least 80%, or at least 90%. Similarly, as discussed herein, the term substantially parallel can mean, but not limited to, for example, that the direction of the grooves in the grating patterns are angled, relative to each other, less than 10%, less than 5%, or more particularly less than 2%.

Figure 4A:
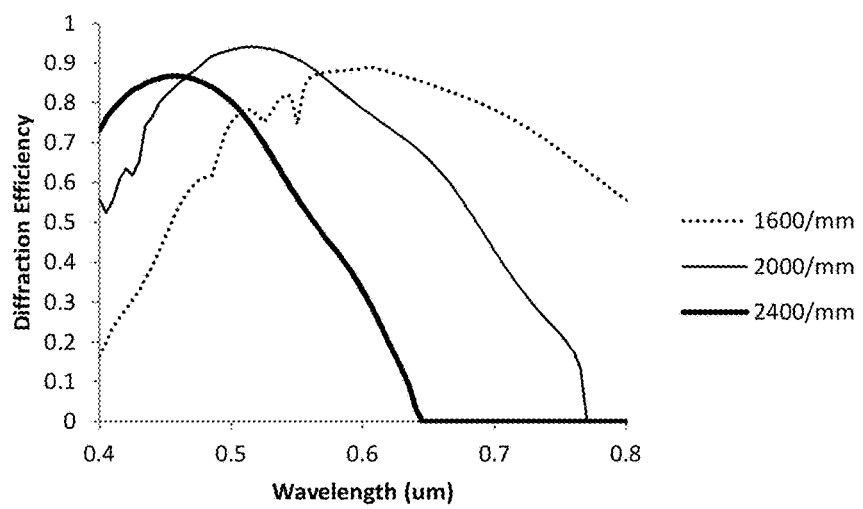
FIGS. 4A and 4B are graphs showing data for three different grating pitches (1600/mm, 2000/mm, and 2400/mm), with FIG. 4A showing a graph of diffraction efficiency versus wavelength, and FIG. 4B showing a graph of diffraction efficiency versus angle of diffraction.
Figure 4B:
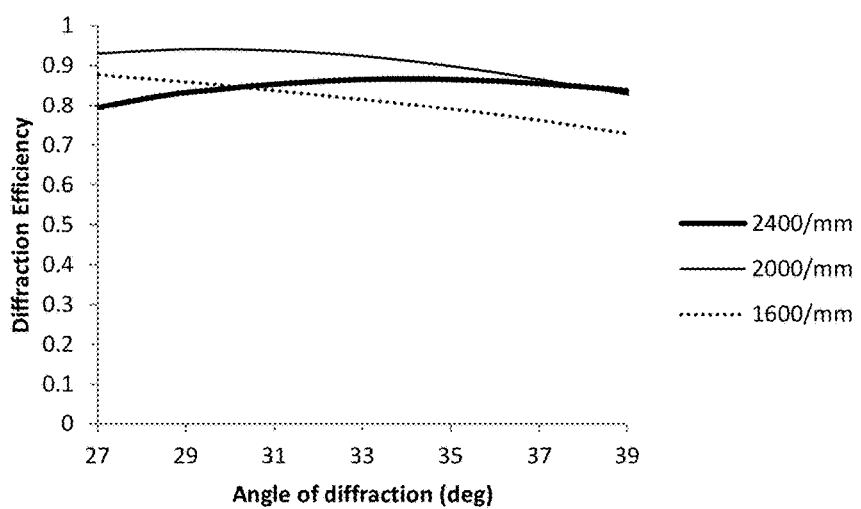

In this exemplary embodiment, the grating refractive index is 1.5037. The incident angle into the grating surface can be about or exactly 20.94 degrees. The groove depth can be about or exactly 900 nm for all three grating patterns, and the duty cycle of each pattern can be about or exactly 0.5. The 1600, 2000 and 2400 lines/mm gratings can diffract light of wavelength 619-730 nm (as red), 495-584 nm (as green) and 413-487 nm (as blue) to the same range of diffraction angle (27-39 degrees), respectively. Exemplary graphs of calculated diffraction efficiency of the three gratings vs. wavelength and angle of diffraction are shown in FIGS. 4A and 4B, respectively. For example, the calculation method can include, but not limited to, Rigorous Coupled-Wave Analysis (RCWA). Red light 311 with an exemplary wavelength of 675 nm can be diffracted by the region 310 at an angle of 33°. Green light 321 with an exemplary wavelength that can be about or exactly 540 nm can be diffracted by the region 320 to an angle of about or exactly 33°, and blue light 331 with an exemplary wavelength of about or exactly 450 nm can be diffracted by the region 330 to the same diffraction angle. From this example, it is obvious that three different wavelengths can be diffracted to the same direction if the grating can have three regions with distinctive groove densities. As illustrated in FIG. 3, the grating patterns on the three regions 310, 320, and 330 can be designed using the exemplary method as described herein to provide appropriate diffraction efficiencies for respective working wavelengths.

Figure 5A:
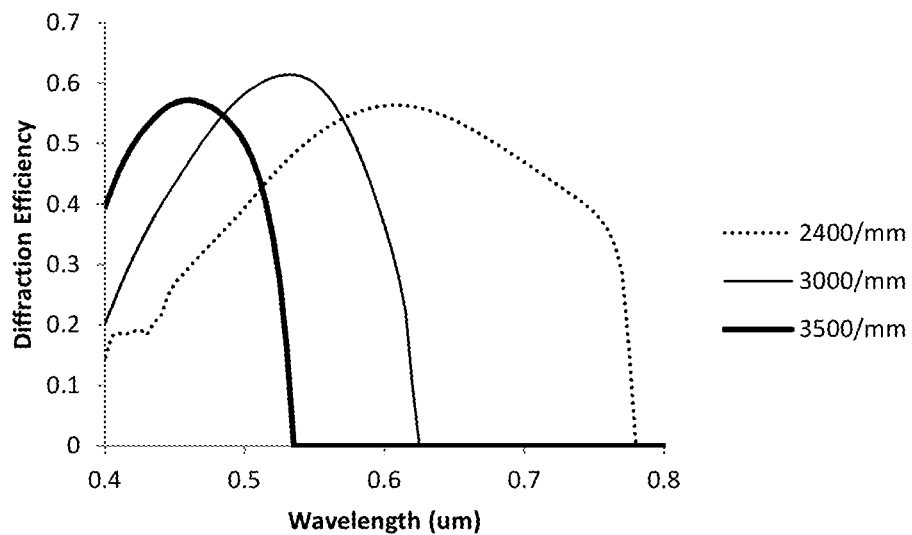
FIGS. 5A and 5B are graphs showing data for three different grating pitches (2400/mm, 3000/mm, and 3500/mm), with FIG. 5A showing a graph of diffraction efficiency versus wavelength, and FIG. 5B showing a graph of diffraction efficiency versus angle of diffraction.
Figure 5B:
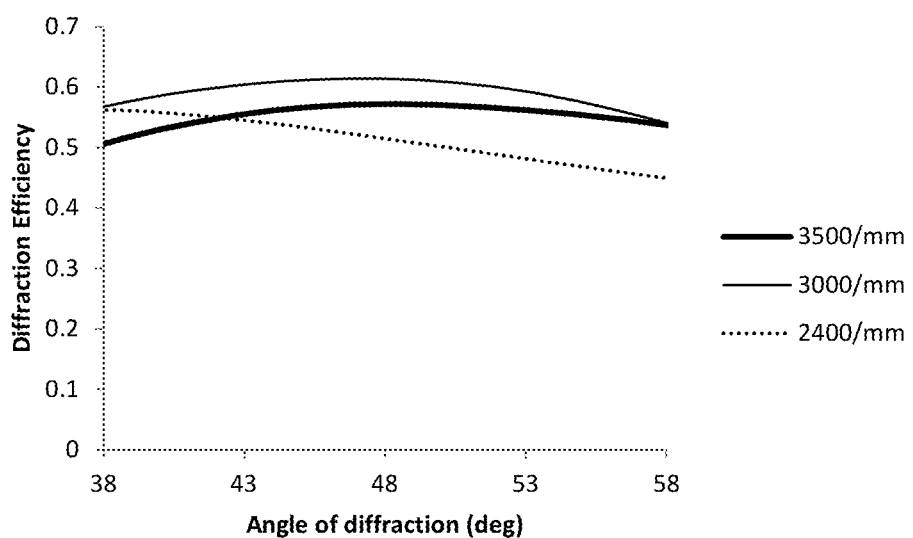

In another example, exemplary gratings of 2400, 3000 and 3500 lines/mm can be used to diffract light of wavelength 615-713 nm (as red), 492-571 nm (as green) and 422-489 nm (as blue) to the same range of diffraction angle (38-58 degrees), respectively, when the grating refractive index is about or exactly 1.5037 and the incident angle to the gratings is about or exactly 35 degrees. Exemplary graphs of variations of diffraction efficiency of the three gratings versus wavelength and angle of diffraction are shown in FIGS. 5A and 5B, respectively. In these exemplary graphs, the duty cycle of the patterns (air part) is about or exactly 0.4, and the groove depth is about or exactly 800 nm.

Various exemplary embodiments can provide the use of two, three, four, or more grating patterns. According to other various exemplary embodiments, the groove densities in the various regions of the grating can be adapted to reflect two, three, or more specified wavelengths of light at the same or similar diffraction angles (e.g., within 5°, 4°, 3°, 2°, 1° or less of each other for the specified wavelengths).

Exemplary groove depth can be different between different gratings in order to optimize diffraction efficiency and/or to make their fabrication easy. For example, grating 120 can have grating patterns 310 (e.g., groove density: 1600 lines/mm, groove depth: 1000 nm), 320 (e.g., groove density: 2000 lines/mm, groove depth: 900 nm), and 330 (e.g., groove density: 2000 lines/mm, groove depth: 800 nm). To make such a grating or its replication master, reactive ion etching (RIE) can be used. In RIE, micro-loading effect is known, i.e., etching through wide opening etching mask is faster than through narrow opening etching mask, which can enable fabrication of three diffraction gratings with different groove depths. Incident angle can be optimized for diffraction efficiency and view angle of SEE probe.

Figure 6A:
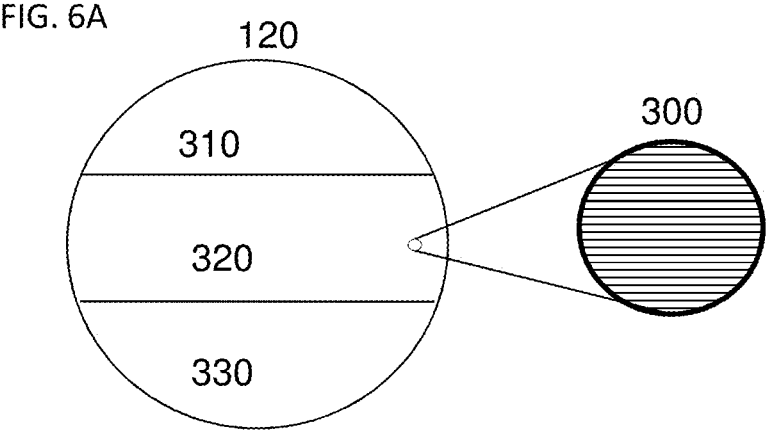
FIGS. 6A-6C are cross-sectional diagrams of an exemplary grating according to an exemplary embodiment of the present disclosure.
Figure 6B:
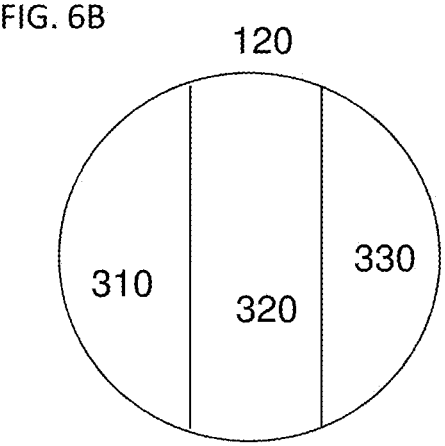
Figure 6C:
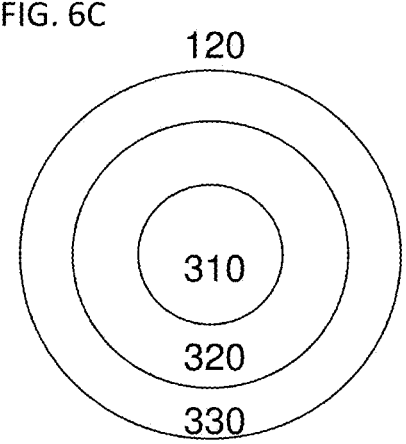

FIGS. 6A-6C show cross-sectional diagrams of exemplary gratings 120 according to an exemplary embodiment of the present disclosure. An exemplary grading according to one exemplary embodiment shown in FIG. 6A has three grating regions 310, 320, and 330 that are spaced vertically, while the grooves of the grating run along the horizontal direction as shown in the magnified view 300 of the grating region. In other exemplary embodiments, the three gratings regions can be spaced horizontally (see FIG. 6B) or radially (see FIG. 6C).

Figure 7A:
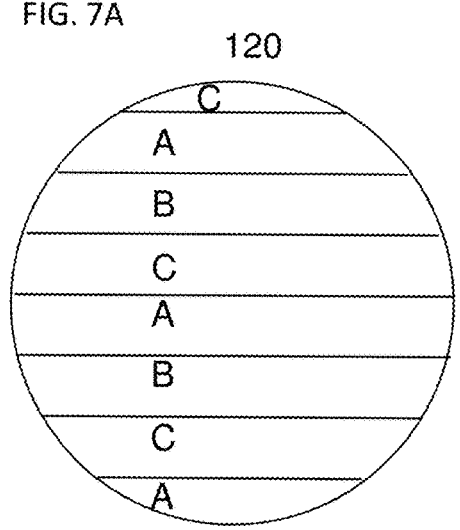
FIGS. 7A-7C are cross-sectional diagrams of the exemplary grating according to another exemplary embodiment of the present disclosure.
Figure 7B:
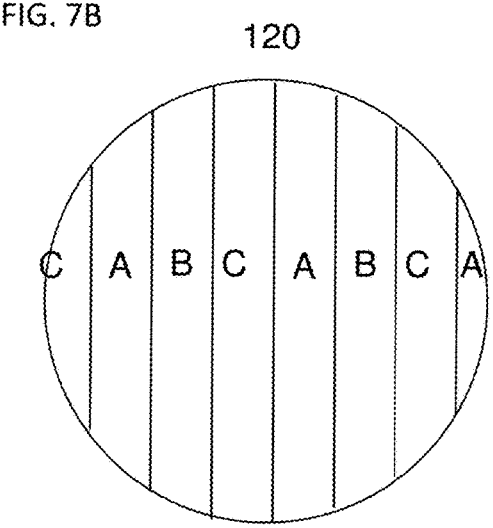
Figure 7C:
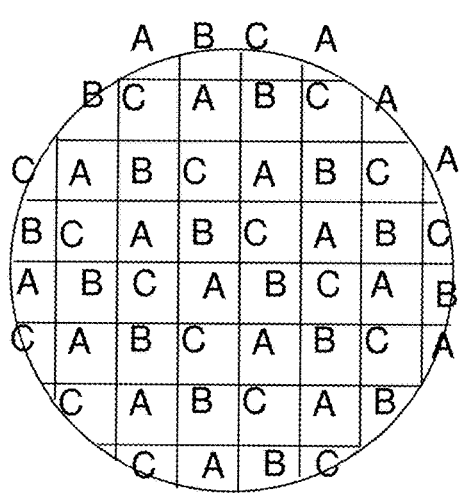

FIGS. 7A-7C show other exemplary embodiments of the gratings 120 according to the present disclosure. The three grating regions can be interlaced vertically (see FIG. 7A) or horizontally (see FIG. 7B). The three grating regions can also be interlaced along both vertical and horizontal directions (see FIG. 7C). These exemplary designs can have an advantage that precise alignment between grating patterns and grating outer shape is not necessary when grating is fabricated.

Figure 8:
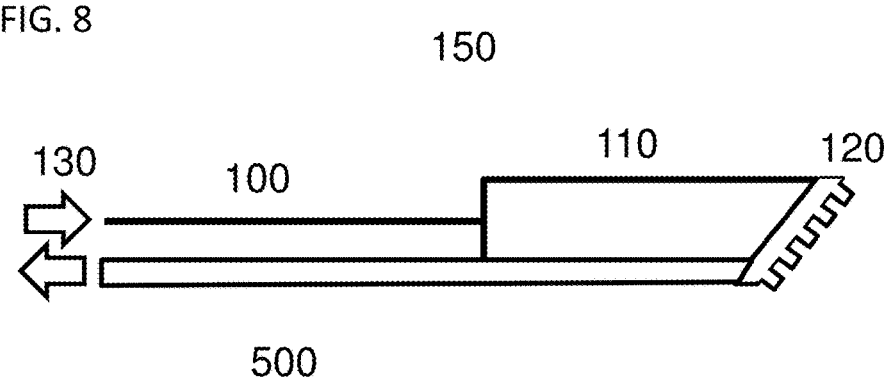
FIG. 8 is a schematic diagram of an exemplary SEE probe according to an exemplary embodiment of the present disclosure in a first exemplary configuration.

FIG. 8 shows a schematic diagram of an exemplary SEE probe according to an exemplary embodiment of the present disclosure that includes an additional fiber for detection. For example, the additional fiber 500 can be employed in the SEE probe to detect light from the specimen. The additional detection fiber 500 can be connected via the grating 120.

This can make the nominal angle of detection aligned with the nominal angle of illumination. The detection fiber 500 can be a multi-mode fiber. In certain exemplary embodiments, a grating can be provided on the detection fiber having patterns with all groove density of the grating on illumination path.

Figure 9:
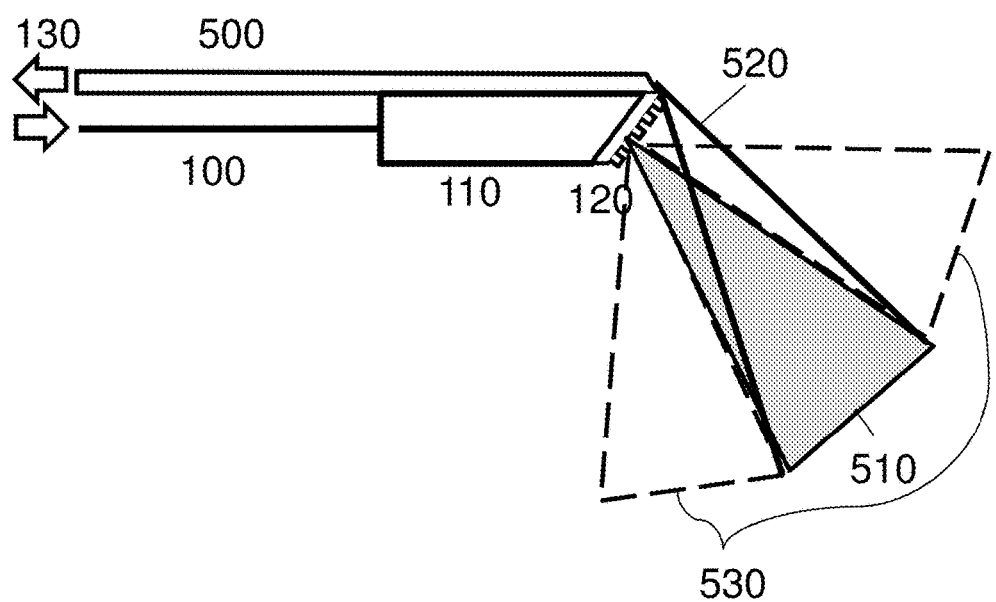
FIG. 9 is a schematic diagram of the exemplary SEE probe shown in FIG. 8 in a second exemplary configuration.

FIG. 9 shows an exemplary SEE system that can include the SEE probe of FIG. 8 according to an exemplary embodiment of the present disclosure. The distal end of the detection fiber 500 can be angle polished to make a detection cone 520 coincide with a illumination cone 510. During the illumination process, an illumination can be provided outside the intended illumination cone 510, shown as 530. Coincidence of the detection cone 520 and intended illumination cone 510 can reject the light from the region 530. Instead of angle-polishing the fiber 500 obliquely, it is possible to put a prism or a mirror on the fiber 500 to the same purpose. The detection fiber can be a multi-mode fiber. Numerical aperture (NA) of the multi-mode fiber and the angle of polishing/prism/mirror can be optimally selected in order to limit the detection field angle to a smaller value than illumination field angle. In other words, the detection fiber 500 can be configured to accept a reflected light from the tissue, e.g., only from region of interest, for example, from the region where multiple lights of different wavelength are illuminated (e.g., the intended illumination cone 510).

Figure 10:
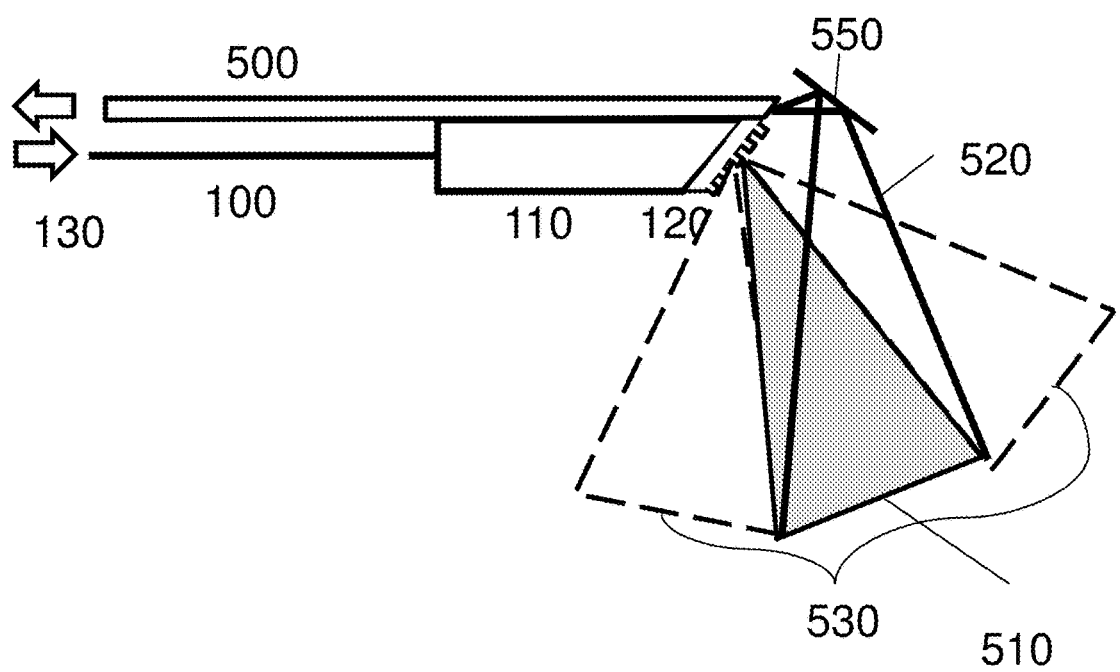
FIG. 10 is a schematic diagram of the exemplary SEE probe shown in FIG. 8 in a third exemplary configuration.

For example, when the NA of the multi-mode fiber is about 0.1 and its polish angle is about 0 degree, the detection fiber 500 can be configured to accept light from the direction between ±5.7 degrees to the optical axis. When the NA is approximately 0.1 and its polish angle is about 35 degrees, the detection fiber 500 can be configured to accept light from the direction between 15.9 and 35.1 degree to the optical axis. There are a number of ways to adjust the detection field to the illumination field. For example, a mirror 550 can be used in front of the detection fiber 500, as shown in FIG. 10. A prism, angle-polished fiber as a mirror surface, and/or other optical components can be used for this purpose as well.

The grating 120 can be fabricated in several ways. For example, the grating 120 can be made by, for example, lithography, including soft-lithography and nanoimprint lithography, which is described in concurrently filed application and claims priority to U.S. Provisional Application Ser. No. 61/934,421, or holography. It is within the scope of the present disclosure to make patterns of the grating 120 prior to integration with a probe. In another exemplary embodiment, it is possible to make various patterns of the grating 120 on the probe.

Thus, there is provided a particularly advantageous color SEE probe and system. The described exemplary embodiments of the grating can be made and used within a small diameter endoscopic probes. For example, the exemplary grating may have a diameter of, for example, less than 500 μm, or less than 350 μm. This exemplary configuration can be useful for in vivo applications.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used in connection with SEE or other imaging systems including those referenced above in U.S. Pat. Nos. 7,843,572; 8,145,018; 6,341,036; 7,796,270; and U.S. Patent Application Publication Nos. 2008/0013960 and 2011/0237892. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A probe comprising:
an illumination optical fiber;
a light focusing configuration;
a grating configuration comprising a first grating pattern and a second grating pattern, and
a detection optical fiber positioned such that a reflected light reflected by a tissue is incident on the detection optical fiber without previously traveling through the grating configuration,
wherein the illumination optical fiber is configured and structured to cause a propagation of a light having a first wavelength and a light having a second wavelength to propagate from the illumination optical fiber, and the light focusing and illumination optical fiber provide the light to be incident on the grating configuration,
wherein the grating configuration is configured and arranged such that the light having the first wavelength is diffracted by the first grating pattern to substantially the same location as the light having the second wavelength is diffracted by the second grating pattern.

2. The probe of claim 1, wherein the first grating pattern and the second grating pattern have different groove densities.

3. The probe of claim 2, wherein the groove densities of the first and second grating pattern differ from one another by at least 200 lines/mm.

4. The probe of claim 1, wherein the first and second grating patterns are substantially parallel to each other.

5. The probe of claim 1, wherein the grating configuration is configured and arranged such that the light having a third wavelength is diffracted by a third grating pattern to substantially the same location as the diffracted light at the first wavelength and the diffracted light at the second wavelength.

6. The probe of claim 5, wherein the first, second and third grating patterns are substantially parallel to each other.

7. The probe of claim 1, wherein the first and second grating patterns are repeated at least two times each on the grating configuration.

8. The probe of claim 1, wherein the portion of the grating configuration positioned in front of the detection optical fiber, in an optic path of the light, has the at least the first grating pattern and the second grating pattern that are repeated at least two times each.

9. The probe of claim 1, wherein the field angle of a light entering the detection optical fiber is smaller than the field angle of the diffracted light having the first wavelength and the diffracted light having the second wavelength.

10. The probe of claim 1, further comprising an optical element positioned such that a light reflected by a tissue reflects off or is angled by the optical element before it is incident on the detection optical fiber.

11. The probe of claim 1, wherein the detection optical fiber comprises an angle-polished optical fiber configured such that the detection field of the detection optical fiber substantially overlaps the illumination field of the probe.

12. A spectrally encoded probe comprising:
an illumination optical fiber;
a light focusing configuration;
a grating configuration comprising a first region having a first grating pattern and a second region having a second grating pattern, the first grating pattern being different from the second grating pattern; and
a detection optical fiber,
wherein the illumination optical fiber is configured and structured to cause a propagation of a light having a first wavelength component and a light having a second wavelength component to propagate from the illumination optical fiber, and the light focusing configuration and illumination optical fiber provide the light to be incident on the grating configuration,
wherein the grating configuration is configured and arranged such that the light having the first wavelength is diffracted by the first grating pattern to substantially the same location as the light having the second wavelength is diffracted by the second grating pattern; and
wherein each of the first grating pattern and second grating pattern are configured and arranged to forward a spectrally-dispersed light.

13. A probe comprising:
an illumination optical fiber;
a light focusing configuration; and
a grating configuration comprising a first region having a first grating pattern and a second region having a second grating pattern different from the first grating pattern,
wherein the illumination optical fiber is configured and structured to cause a light having a first wavelength and a light having a second wavelength to be incident on the grating configuration; and
wherein the grating configuration is configured and arranged such that the light having the first wavelength is diffracted by the first region to substantially the same location as the light having the second wavelength component diffracted by the second grating region.

14. The probe of claim 13, wherein the first and the second grating patterns are different from each other in groove densities.

15. The probe of claim 13, wherein the first and second grating patterns are different from each other in groove depth.

* * * * *